(12) United States Patent
Rottenberg et al.

(10) Patent No.: US 10,299,662 B2
(45) Date of Patent: May 28, 2019

(54) ENDOSCOPIC SLEEVE

(71) Applicant: ENDOAID LTD., Caesarea (IL)

(72) Inventors: Dan Rottenberg, Haifa (IL); Omer Shezifi, Haifa (IL)

(73) Assignee: Endoaid Ltd., Caesarea Business Park (IL)

( * ) Notice: Subject to any disclaimer, the term of this patent is extended or adjusted under 35 U.S.C. 154(b) by 1174 days.

(21) Appl. No.: 14/118,234

(22) PCT Filed: Jun. 6, 2013

(86) PCT No.: PCT/US2013/044407
§ 371 (c)(1),
(2) Date: Nov. 17, 2013

(87) PCT Pub. No.: WO2014/123563
PCT Pub. Date: Aug. 14, 2014

(65) Prior Publication Data
US 2015/0148606 A1    May 28, 2015

(51) Int. Cl.
*A61B 1/00* (2006.01)
*A61B 1/04* (2006.01)
*A61B 1/31* (2006.01)
*A61B 17/02* (2006.01)
*A61B 17/00* (2006.01)

(52) U.S. Cl.
CPC ...... *A61B 1/00135* (2013.01); *A61B 1/00087* (2013.01); *A61B 1/00101* (2013.01); *A61B 1/31* (2013.01); *A61B 17/0218* (2013.01); *A61B 2017/00296* (2013.01); *A61B 2017/00902* (2013.01)

(58) Field of Classification Search
None
See application file for complete search history.

(56) References Cited

U.S. PATENT DOCUMENTS

| | | |
|---|---|---|
| 2002/0156454 A1 | 10/2002 | Raydel |
| 2003/0018307 A1 | 1/2003 | Raydel |
| 2007/0282255 A1 | 12/2007 | Salemi |
| 2011/0087070 A1* | 4/2011 | Tilson ............ A61B 1/00135 600/121 |
| 2013/0090527 A1* | 4/2013 | Axon ............ A61B 1/00075 600/114 |

FOREIGN PATENT DOCUMENTS

| | | |
|---|---|---|
| GB | 2478081 | 8/2011 |
| JP | 2003 339631 | 12/2003 |
| WO | 00/13736 | 3/2000 |

OTHER PUBLICATIONS

PCT Written Opinion PCT/US2013/044407, dated Aug. 9, 2013.

* cited by examiner

*Primary Examiner* — Alexandra L Newton
(74) *Attorney, Agent, or Firm* — Dekel Patent Ltd.; David Klein

(57) ABSTRACT

An endoscopic sleeve includes a tubular member from which spaced projecting elements. The projecting elements are bendable towards both proximal and distal directions of the tubular member. The force (insertion force) required to bend the projecting elements towards the proximal direction is less than a force (extraction force) required to bend the projecting elements towards the distal direction. An outer periphery of the projecting elements decreases as the extraction force increases.

13 Claims, 6 Drawing Sheets

ENDOSCOPIC SLEEVE

FIELD OF THE INVENTION

The present invention relates to a sleeve or cuff having external projections, e.g., full or partial rings or wings, for use with medical endoscopes, particularly but not exclusively, a colonoscope.

BACKGROUND OF THE INVENTION

In endoscopic examinations/procedures, flexible instruments are used to view a body lumen, such as the gastrointestinal tract and many others. The instruments are provided with fiber optic or charge-couple device (CCD) cameras which enable images to be transmitted around bends and images to be produced to displays on a screen.

For example, colonoscopic and enteroscopic examinations are the most effective techniques to assess the state of health of the bowel. However, they are inconvenient, uncomfortable, expensive procedures that are associated with significant risks of potentially serious complications. A further disadvantage is that they are time consuming for patients and medical personnel alike.

Four yet further additional significant difficulties associated with colonoscopy and scoping procedures more generally are as follows:

Firstly, the anatomy of the colon is such that the lining is thrown into folds. As the tip of the endoscope passes along the lumen of the colon, these folds hamper the endoscopist's ability to visualize the entire surface of the mucosa and in particular, detect pre-malignant and malignant lesions tucked away on the proximal face of these folds during extubation.

Secondly, the position of the tip may be difficult to maintain from the moment at which a lesion or polyp is detected to the completion of any therapeutic procedure. As the colonoscope is moving the tip does not travel back at a constant speed but rather with jerks and slippages particularly when traversing a bend or length of colon where the bowel has been concertinaed over the endoscope shaft during intubation. The tip of the device may, at any moment, slip backwards thereby causing the clinician to lose position. If tip position is lost, the clinician is required to relocate the lesion or polyp for the therapeutic procedure to be continued.

Thirdly, bowel tissue is flexible and may fall over the scope distal end, disturbing the camera view/video picture.

Fourthly, fecal and liquid remains may hide the colon walls, preventing proper examination of the colon tissue.

The colonoscopic procedure is not simple because the bowel is long and convoluted. In places it is tethered by peritoneal bands and in others it lies relatively free. When the tip of the endoscope encounters a tight bend the free part of the colon "loops" as more of the endoscope is introduced and causes difficulty to negotiate the bend.

PCT Patent Application WO 2011/148172 describes a sleeve for a medical scope distal section. The sleeve has a plurality of moveable, external, angled projecting elements having a tip and a base, which are moveable between a resting angled position to a position wherein the tip of the projecting element is substantially parallel to a longitudinal axis of the medical scope, and to a position that is at an angle approximately perpendicular to the longitudinal axis of the medical scope. The device is intended to close the projection elements while the medical scope is moving forward (distally), and open the projection elements during withdrawal of the medical scope (proximally), thereby to assist opening colon folds for better colon mucosa examination during scope withdrawal (only). Since bowel screening is not usually done in one withdrawal movement but in short movements backwards and forward, such projection elements may not reach a perpendicular position relative to the longitudinal axis of the medical scope.

PCT Patent Application WO00/13736 describes an apparatus for percutaneous insertion into the cardiovascular system. It includes a catheter or catheter guide having a distal end, and flexible, permanently extended, generally radial protrusions (e.g., thin flexible fins or radially spaced fins) situated adjacent the distal tip of the catheter.

SUMMARY

Reference herein to a "medical scoping device" is intended to encompass endoscopes, enteroscopes, gastroscopes, colonoscopes and other types of scopes, and is used interchangeably and is intended to include all scoping instruments inserted into or through a body/organ/tissue lumen or cavity (used interchangeably). Endoscopy involves the inspection and treatment of the inside of the body lumen or cavity.

There is provided in accordance with an embodiment of the invention, an endoscopic sleeve that includes a tubular member from which extend a plurality of spaced projecting elements. The projecting elements are bendable towards both proximal and distal directions of the tubular member. The force (insertion force) required to bend the projecting elements towards the proximal direction is less than a force (extraction force) required to bend the projecting elements towards the distal direction. An outer periphery of the projecting elements decreases as the extraction force increases. The projecting elements may be more bendable towards the proximal direction than towards the distal direction.

The projecting elements may be moveable between at least three positions. In a first position the projecting elements protrude freely, at an angle, such as perpendicular, to the longitudinal axis of the endoscope (so called "resting position"). In a second position, when the sleeved endoscope is introduced distally into a body lumen, insertion forces act upon the thin projecting elements to push them proximally backwards towards the shaft of the endoscope so that they may become tilted or even substantially parallel to the longitudinal axis of the endoscope, reducing the total device and sleeve diameters. In a third position, when the endoscope is withdrawn in a proximal direction out of the patient lumen, the thin projecting elements are bent by extraction forces, this time to the other direction (distally). The projecting elements fan out and extend from the shaft of the endoscope so as to gently contact or grip the inner surface of the body lumen. During extraction, the total device and sleeve diameters also decrease.

The projecting elements may be multiple thin rings (partial or full) or wings that are arranged circumferentially around the sleeve and along the length of the sleeve. Without limitation, there may be between 2 and 30 projecting elements. It will be appreciated that the projecting elements may, in some embodiments, be provided as a single ring. Each projecting element may have the same thickness, or different projecting element may have different thicknesses. The projecting element may have a variable thickness along its extended outward diameter or its perimeter. Without limitation, each projecting element can have an outer diameter between 20 to 60 mm, and more preferably between 30 to 50 mm, with a thickness between 0.2 to 2.0 mm, and more preferably between 0.3 to 1.0 mm. All projecting elements may have the same diameter, or different projecting elements may have different diameters. Projecting elements may be spaced apart by a distance of between 1 to 10 mm and more preferably 2 mm to 5 mm. Different sizes of gaps may be used for different projecting elements.

BRIEF DESCRIPTION OF THE DRAWINGS

Embodiments of the invention are further described hereinafter with reference to the accompanying drawings, in which:

FIGS. 6A and 6B are simplified top-view and side-view illustrations, respectively, of an endoscopic sleeve, constructed and operative in accordance with another embodiment of the invention, in which the projecting elements are discrete wings, and in which FIG. 6B illustrates proximal projecting elements bent distally against unbent distal projecting elements;

DETAILED DESCRIPTION

Figure 1:
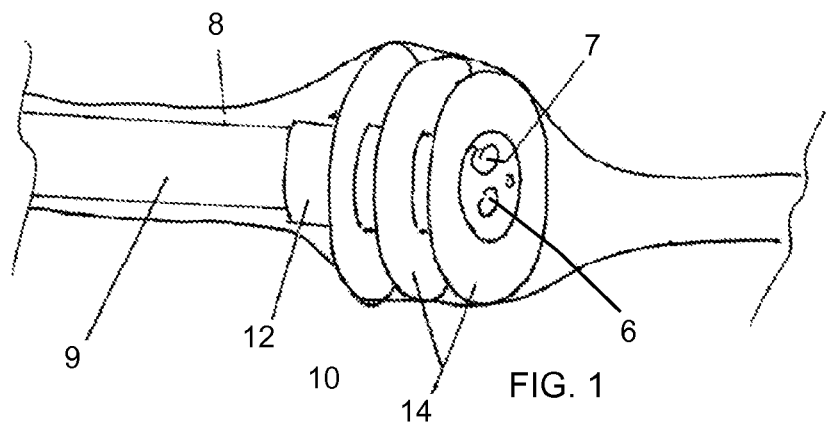
FIG. 1 is a simplified illustration of an endoscopic sleeve, constructed and operative in accordance with an embodiment of the invention, mounted on an endoscope and inserted in a body lumen.

Reference is now made to FIG. 1, which illustrates an endoscopic sleeve 10, constructed and operative in accordance with an embodiment of the invention, mounted on an endoscope 9 and inserted in a body lumen 8, such as but not limited to, the colon or other parts of the GI tract or other body lumens. Endoscope 9 has one or more image capturing devices 7 for viewing the body lumen and working lumens 6 (such as for introducing tools to collect tissue samples, or for irrigation or suction, etc.), as is well known in the art.

Sleeve 10 is arranged for mounting over the distal end of the shaft of endoscope 9 so as to surround (or partially surround) and extend along at least a distal part or tip region of the endoscope shaft.

In a non-limiting embodiment of the invention, endoscopic sleeve 10 includes a tubular member 12 from which extend a plurality of spaced projecting elements 14. Projecting elements 14 are bendable towards both proximal and distal directions of tubular member 12. As will be explained further hereinbelow, projecting elements 14 are more bendable towards the proximal direction than towards the distal direction. In the illustrated embodiment, projecting elements 14 are full rings or partial rings, and are initially generally perpendicular to tubular member 12.

All components of sleeve 10 are constructed of a suitable biocompatible material so that they are flexible, resilient and deformable. Examples of suitable materials include, but are not limited to, polymers, elastomers and rubbers, such as polyurethane, natural rubber, silicone and silicone elastomeric materials. The material is preferably transparent to be able to hold tissue and still allow visualization.

Tubular member 12 and projecting elements 14 may be made of the same material or different materials. Some of the projecting elements 14 may be made of different materials than other projecting elements 14.

Figure 5:
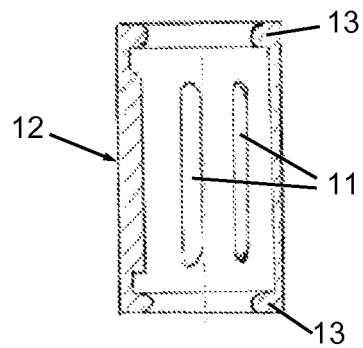
FIG. 5 is a simplified illustration of an endoscopic sleeve with seals at its distal and proximal ends, in accordance with an embodiment of the invention.

As seen in FIG. 5, distal and proximal portions of tubular member 12 may have seals 13, such as 0-rings. The seals 13 help tubular member 12 from slipping off the endoscope because they prevent fluids from coating the outer periphery of tubular member 12. Tubular member 12 may also be provided with elongate, longitudinal stiffening ribs 11, which maintain the structural integrity of member 12 when it is slipped over the end of the endoscope. In other words, ribs 11 prevent member 12 from kinking or otherwise deforming, which would make it difficult to slip the member 12 over the scope.

Figure 2A:
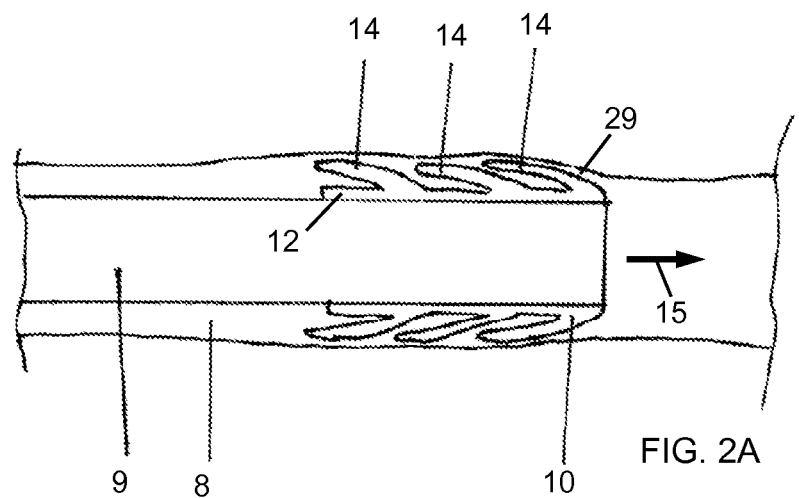
FIGS. 2A and 2B are simplified illustrations of the endoscopic sleeve and endoscope, respectively during distal motion and proximal motion of the endoscope in the body lumen, in accordance with an embodiment of the invention.

Reference is now made to FIG. 2A, which illustrates endoscopic sleeve 10 and endoscope 9 during distal motion (such as insertion) in the body lumen 8, as indicated by arrow 15, the projecting elements 14 bend backwards proximally and can be generally parallel to tubular member 12. In this manner, projecting elements 14 do not hinder distal progression of the endoscope in the body lumen.

Figure 2B:
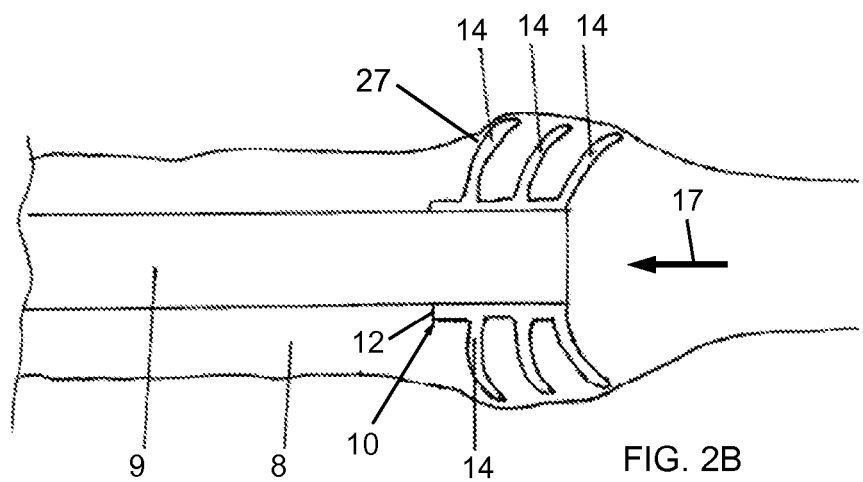

In FIG. 2B, endoscopic sleeve 10 and endoscope 9 are moved proximally (such as during retraction or during reciprocating motion of the endoscope) in the body lumen 8, as indicated by arrow 17. During proximal motion of the endoscope in the body lumen, projecting elements 14 sufficiently project away from tubular member 12 so as to contact and unfold tissue folds in body lumen 8 for improved endoscopic visualization of the folds.

Figure 3A:
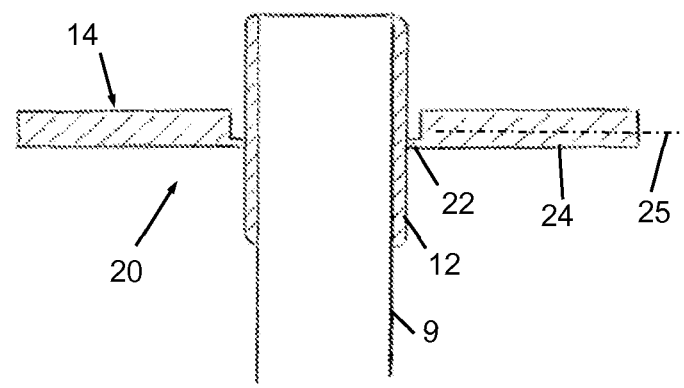
FIGS. 3A, 3B and 3C are simplified illustrations of an endoscopic sleeve, constructed and operative in accordance with an embodiment of the invention, wherein projecting elements of the endoscopic sleeve are generally perpendicular to a tubular member of the sleeve (FIG. 3A), or bent towards the proximal direction (FIG. 3B) or bent towards the distal direction (FIG. 3C)
Figure 3B:
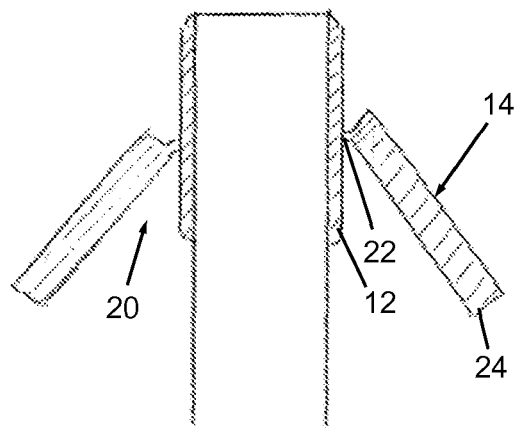
Figure 3C:
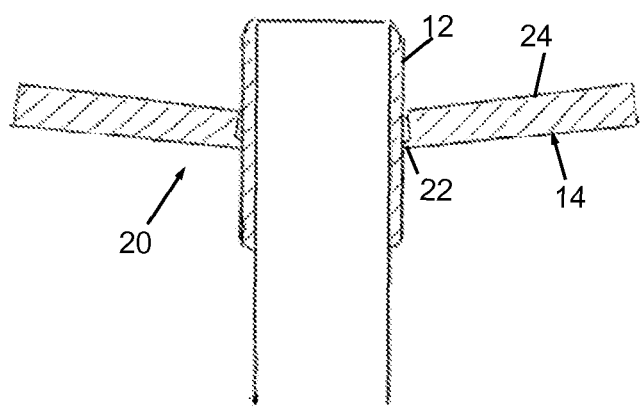

Reference is now made to FIGS. 3A-3C, which illustrate an endoscopic sleeve 20, constructed and operative in accordance with an embodiment of the invention. In the illustrated embodiment, each of the projecting elements 14 has a root portion 22 that extends from tubular member 12 and a tissue interface portion 24 that extends outwards from root portion 22. Root portion 22 is thinner than tissue interface portion 24 and is offset proximally from a centerline 25 of tissue interface portion 24. As is seen by comparing FIGS. 3B and 3C, bending of projecting elements 14 towards the proximal direction is not limited (FIG. 3B); however, bending towards the distal direction is limited by tissue interface portion 24 abutting against tubular member 12 (FIG. 3C).

Figure 4:
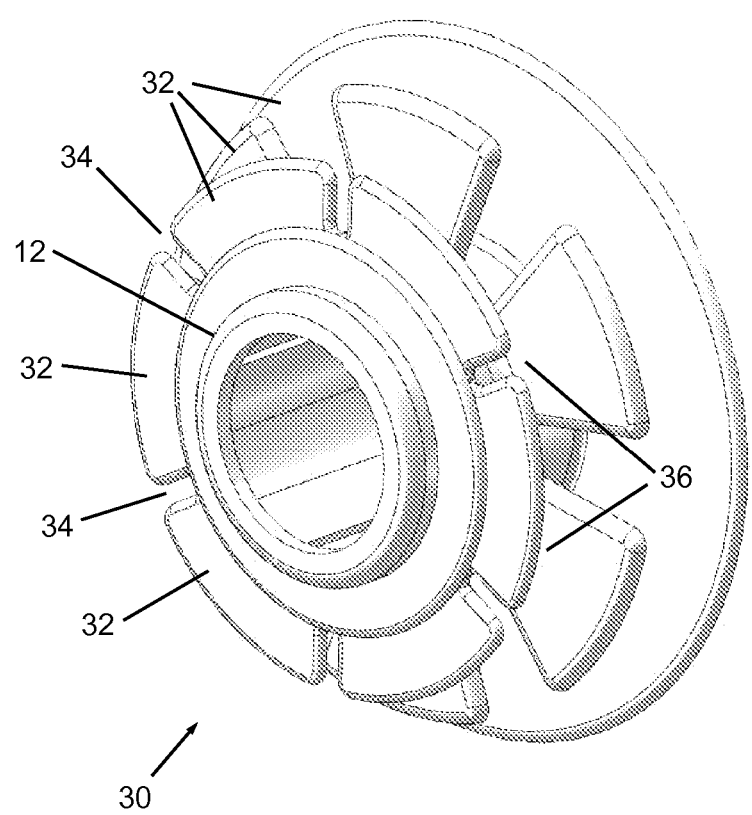
FIG. 4 is a simplified illustration of an endoscopic sleeve, constructed and operative in accordance with another embodiment of the invention, including projecting elements (wings) that are more bendable towards the proximal direction than towards the distal direction.

This structure may be used for rings, partial rings, wings and any other type of projecting element (such as the embodiment of FIG. 4). One of the advantages of this structure is it provides little or no resistance to inserting the endoscope into the body lumen, but when retracting the endoscope proximally, provides a greater resistance to endoscope movement that opens tissue folds, centers the endoscope, and improves imaging of the internal structure of the body lumen during endoscope retrieval. The projecting elements 14 fan out and extend from the tubular member 12 so as to gently contact or grip the inner surface of the body lumen. Accordingly, the force (i.e., the insertion force) required to bend the projecting elements 14 towards the proximal direction is less than the force (i.e., the extraction force) required to bend the projecting elements 14 towards the distal direction. The outer periphery of the projecting elements 14 decreases as the extraction force increases.

The tissue interface portion may have a bulged or roughened surface 27 (an example is shown in FIG. 2B) for enhanced engagement with tissue folds. Some of the projecting elements 32 may have a thicker base 29 that joins tubular member 12, which tapers in a direction away from tubular member 12 (an example is shown in FIG. 2A).

Reference is now made to FIG. 4 is a simplified illustration of an endoscopic sleeve 30, constructed and operative in accordance with another embodiment of the invention. In this embodiment, the projecting elements 32 are discrete wings, which, as with the other embodiments of the invention, are more bendable towards the proximal direction than towards the distal direction. Wings 32 are spaced from one another by gaps 34 about a periphery of the tubular member 12.

There are sets of projecting elements 32, each set spaced axially from one another (along the longitudinal length of tubular member 12). As seen in the illustrated embodiment, one or more of the sets may have discrete wings and one or more of the sets may be a full or partial ring (e.g., the most proximal projecting element). Progressing proximally along the length of tubular member 12, the sets of projecting elements 32 are gradually larger in a radial direction extending out from tubular member 12 (that is, elements 32 jut out more radially as one progresses proximally such that the most distal set juts out the least and the most proximal set juts out the most).

In one embodiment, the gaps 34 of one set of the projecting elements 32 are angularly offset in a circumferential direction from gaps 34 of an adjacent set of projecting elements 32. The more proximal set of projecting elements 32 is hindered in bending towards the distal direction by abutting against the more distal set of projecting elements 32. For example, the more proximal set of projecting elements 32 includes an abutting portion 36 arranged to abut against the more distal set of projecting elements 32. The abutting portion 36 is wider than the gap 34 between projecting elements 32 of the more distal set of projecting elements 32.

This structure provides strong bending resistance when pulling the endoscope proximally backwards, because the layer of the larger-diameter proximal projection elements bends and abuts against the adjacent, more distal layer which is of a smaller diameter, thus increasing the resistance to the extraction force that pulls the endoscope proximally backwards. The outer diameter of the projecting elements 32 decreases as the extraction force increases. The proximal wings 32 may have a thicker or wider middle section (abutting portion 36), such that when the wings start bending, they abut against the more distal wings, which increases the total bend resistance when proximally pulling the endoscope. In contrast, when inserting the scope in the distal direction, the larger-diameter proximal layer bends in the proximal direction, not leaning on any other layer, and then the smaller, more distal layer also bend proximally; there is no accumulation of bending resistance.

Figure 6A:
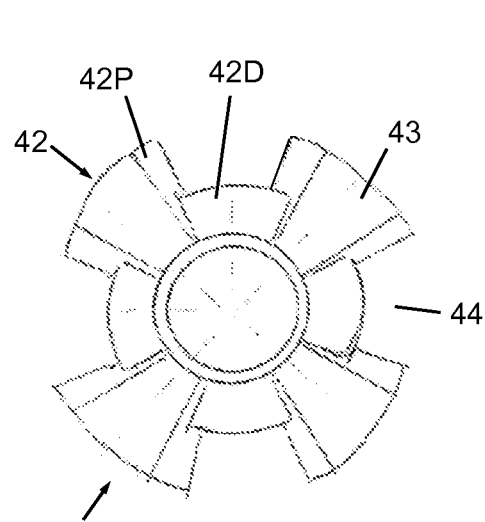
Figure 6B:
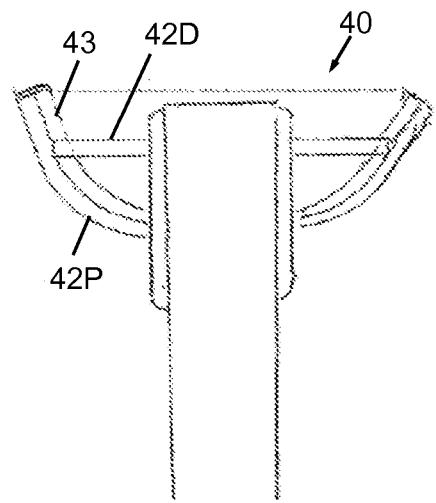

Reference is now made to FIGS. 6A-6B, which illustrate an endoscopic sleeve 40, constructed and operative in accordance with another embodiment of the invention. In this embodiment, the projecting elements 42 are discrete wings, and the more proximal layer of projection elements 42P includes a central, radial crossbeam 43 (abutting portion 43) that effectively thickens the central portion of the projection element.

There are sets of projecting elements 42, each set spaced axially from one another (along the longitudinal length of tubular member 12). As seen in the illustrated embodiment, the sets may have discrete wings. Progressing proximally along the length of tubular member 12, the sets of projecting elements 42 are gradually larger in a radial direction extending out from tubular member 12 (that is, elements 42 jut out more radially as one progresses proximally such that the most distal set juts out the least and the most proximal set juts out the most).

The gaps 44 of one set of the projecting elements 42 are angularly offset in a circumferential direction from gaps 44 of an adjacent set of projecting elements 42. The more proximal set of projecting elements 42P is hindered in bending towards the distal direction by crossbeam 43 filling (and preferably overlapping) the gap 44 between the projection elements 42D of the smaller diameter and more distal layer, so that the more proximal set of projecting elements 42P abuts against the more distal set of projecting elements 42D. This accumulative structure has a stronger bending resistance when pulling the endoscope proximally backwards.

Figure 7:
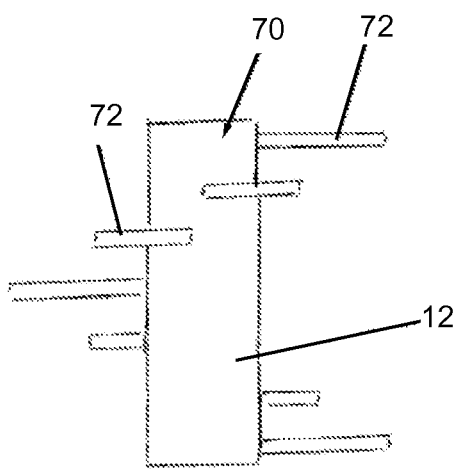
FIG. 7 is a simplified illustration of an endoscopic sleeve, constructed and operative in accordance with another embodiment of the invention, in which projecting elements are spirally offset.

Reference is now made to FIG. 7, which illustrates an endoscopic sleeve 70, constructed and operative in accordance with another embodiment of the invention. In this embodiment, projecting elements 72 are spirally or sporadically offset, that is, they are arranged in a spiral shape around tubular member 12, starting from its distal section until its proximal section. Spirally offset projection elements 72 may allow easier insertion and removal of the scope from the body lumen.

Figure 8:
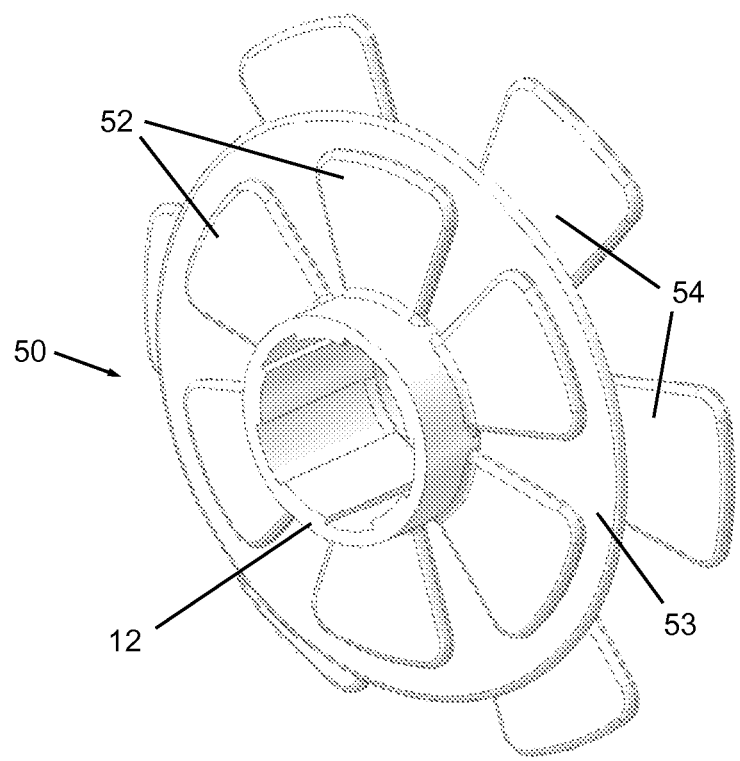
FIG. 8 is a simplified illustration of an endoscopic sleeve, constructed and operative in accordance with another embodiment of the invention, in which distal projecting elements are attached to a full circular ring.

Reference is now made to FIG. 8, which illustrates an endoscopic sleeve 50, constructed and operative in accordance with another embodiment of the invention. In this embodiment, distal projecting elements 52 are attached to full circular ring 53, which is a more stable structure and has greater bending resistance to proximal projection elements 54 bending and abutting against the distal projection elements 52. Proximal projection elements 54 are discrete wings.

Some of projection elements 54 may have smaller diameter then the others, to allow easy turn-over or flipping of the elements 54 from bending backwards during scope insertion, to bending backwards during scope extraction. Very thin flexible film (made from same material) may connect projection elements 54, to support flipping of the larger projection elements 54 after the smaller elements 54 have been flipped.

Figure 9:
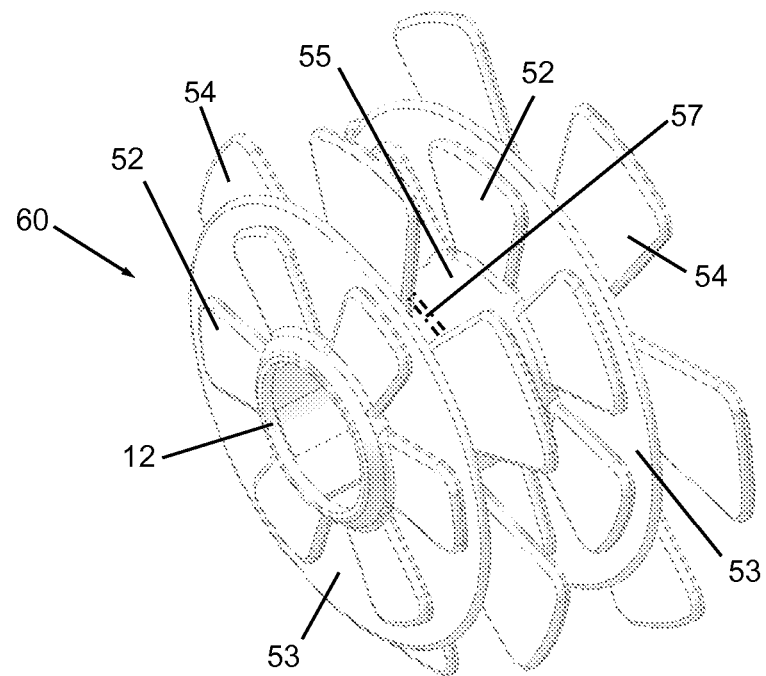
FIG. 9 is a simplified illustration of an endoscopic sleeve, constructed and operative in accordance with another embodiment of the invention, in which there are two sets of projection element layers.

Reference is now made to FIG. 9, which illustrates an endoscopic sleeve 60, constructed and operative in accordance with another embodiment of the invention. Sleeve 60 is similar to sleeve 50, except that sleeve 60 includes two sets of projection element layers, wherein each set includes distal projecting elements 52 attached to ring 53 and proximal projection elements 54. The two sets are separated from each other by a longitudinal gap 55. This gap may be sized to match a tissue fold, such as a fold in the colon, so that when the fold is released from one layer of projection elements, the other may still hold the next fold, thereby providing continued stretching of the colon.

Another option of the invention is shown in broken lines in FIG. 9. A web 57 may be formed between protruding elements, which ensures that all the protruding elements bend together (preventing the situation wherein one element may bend as opposed to an adjacent one which does not bend). The protruding elements may also be of varying sizes and shapes.

Figure 10:
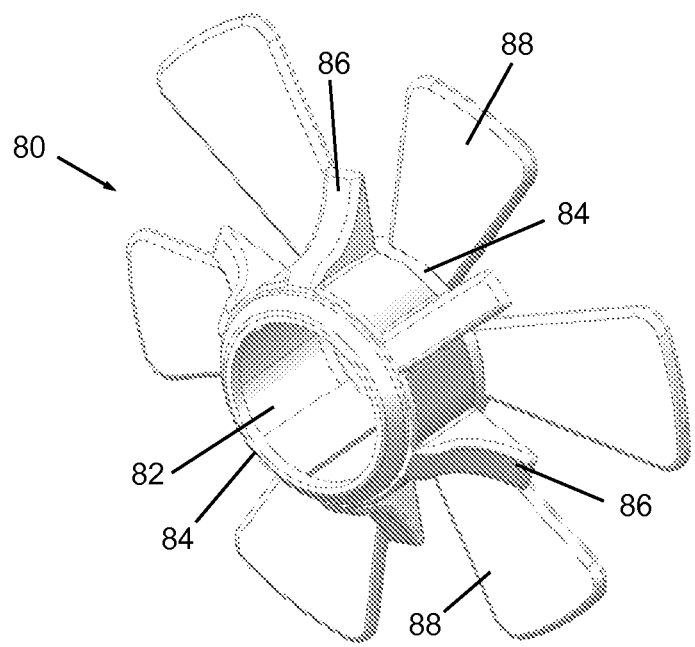
FIG. 10 is a simplified illustration of an endoscopic sleeve, constructed and operative in accordance with another embodiment of the invention, in which a tubular member can rotate freely around the endoscope.

Reference is now made to FIG. 10, which illustrates an endoscopic sleeve 80, constructed and operative in accordance with another embodiment of the invention. In this embodiment, a tubular member 82 is rotatingly supported by two bearing rings 84. In this manner, tubular member 82 can rotate freely around the scope, but is restricted from moving axially by rings 84. Tubular member 82 includes stoppers 86 arranged about the central axis of member 82, typically, but not necessarily, corresponding to the position and number of projection elements 88. If tubular member 82 is rotated such that stoppers 86 are in front of projection elements 88, then stoppers 86 prevent easy bending of projection elements 88, providing high bending resistance. If tubular member 82 is rotated so that stoppers 86 are not in front of projection elements 88, then projection elements 88 can bend much more easily. Thus, the user can rotate tubular member 82 to modify the bending resistance of projection elements 88.

The invention claimed is:

1. A device comprising:
an endoscopic sleeve comprising a tubular member from which extend a plurality of spaced projecting elements, each of which has an initial position, said projecting elements being bendable towards both proximal and distal directions of said tubular member, wherein a force (insertion force) required to bend said projecting elements from said initial positions towards the proximal direction is less than a force (extraction force) required to bend said projecting elements from said initial positions towards the distal direction and a distance all around an outer periphery of said projecting elements decreases as the extraction force increases, and wherein said projecting elements comprise sets of projecting elements, each set spaced axially from one another, and wherein adjacent sets of projecting elements comprise a more proximal set of projecting elements and a more distal set of projecting elements, and the more proximal set of projecting elements is hindered in bending towards said distal direction by abutting against the more distal set of projecting elements.

2. The device according to claim 1, wherein said projecting elements are more easily bendable towards the proximal direction than towards the distal direction.

3. The device according to claim 1, wherein each of said projecting elements comprises a root portion that extends from said tubular member and a tissue interface portion that extends outwards from said root portion, wherein said root portion is thinner than said tissue interface portion and is offset proximally from a centerline of said tissue interface portion, and wherein bending of said projecting elements towards the proximal direction is not hindered and bending of said projecting elements towards the distal direction is hindered by said tissue interface portion abutting against said tubular member.

4. The device according to claim 1, wherein said projecting elements comprise at least partial rings.

5. The device according to claim 1, wherein said projecting elements comprise discrete wings spaced from one another by gaps about a periphery of said tubular member.

6. The device according to claim 1, wherein gaps of one set of said projecting elements are angularly offset in a circumferential direction from gaps of an adjacent set of projecting elements.

7. The device according to claim 1, wherein the more proximal set of projecting elements comprises an abutting portion arranged to abut against the more distal set of projecting elements, said abutting portion being wider than the gap between the projecting elements of the more distal set of projecting elements.

8. The device according to claim 1, wherein said projecting elements have a thicker base joining said tubular member which tapers in a direction away from said tubular member.

9. The device according to claim 1, wherein progressing proximally along a length of said tubular member, said sets of projecting elements are gradually larger in a radial direction extending out from said tubular member.

10. The device according to claim 1, wherein seals are placed at distal and proximal portions of said tubular member.

11. The device according to claim 1, wherein said tubular member comprise elongate, longitudinal stiffening ribs.

12. The device according to claim 1, wherein a web is formed between two of said protruding elements.

13. A method of improving endoscopic visualization comprising installing the endoscopic sleeve of claim 1 on an endoscope and inserting the endoscope in a body lumen, wherein during distal motion of the endoscope in the body lumen said projecting elements bend towards the proximal direction so as not to hinder the distal motion of the endoscope, and during proximal motion of the endoscope in the body lumen said projecting elements sufficiently project away from said tubular member so as to engage and unfold tissue folds in said body lumen for improved endoscopic visualization of said folds.

* * * * *